United States Patent [19]
Faddis et al.

[11] Patent Number: 5,344,622
[45] Date of Patent: Sep. 6, 1994

[54] OZONE STERILIZATION SYSTEM VAPOR HUMIDIFICATION COMPONENT WITH DISPOSABLE WATER SOURCE

[75] Inventors: Chris G. Faddis, West Valley City; Paul O. Shepherd, South Jordan, both of Utah

[73] Assignee: Cyclo$_3$pss Medical Systems, Inc., Salt Lake City, Utah

[21] Appl. No.: 26,025

[22] Filed: Apr. 3, 1993

[51] Int. Cl.$^5$ .............................. A61L 2/02; A61L 2/24
[52] U.S. Cl. .................................... 422/306; 422/108; 422/119; 422/186.2; 219/396; 219/397
[58] Field of Search ............... 422/123, 125, 298, 306, 422/108, 119, 186.2; 122/13.2; 219/386, 394, 396, 397, 403

[56] References Cited

U.S. PATENT DOCUMENTS

| | | | |
|---|---|---|---|
| 3,873,806 | 3/1975 | Schossow | 422/125 |
| 3,897,210 | 7/1975 | Gruber et al. | 422/32 |
| 4,517,159 | 5/1985 | Karlson | 422/30 |
| 4,909,999 | 3/1990 | Cummings et al. | 422/298 |
| 5,069,880 | 12/1991 | Karlson | 422/186.19 |
| 5,087,419 | 2/1992 | Lutz | 422/33 |
| 5,118,471 | 6/1992 | Andersen et al. | 422/34 |
| 5,120,512 | 6/1992 | Masuda | 422/297 |
| 5,266,275 | 11/1993 | Faddis | 422/28 |

*Primary Examiner*—Robert J. Warden
*Assistant Examiner*—T. A. Trembley
*Attorney, Agent, or Firm*—M. Reid Russell

[57] ABSTRACT

A vapor humidification component with a disposable water source for a medical instrument sterilization system that utilizes ozone as a sterilization agent. The humidification component of the invention receives a measured input of water that is vaporized therein and injected into an ozone-oxygen mixture flow for passage into a primary sterilization chamber wherein the humidified ozone-oxygen mixture is circulated to scour and sterilize, during a sterilization cycle, medical instruments contained therein, whereafter the ozone-oxygen mixture is passed to a destruction chamber for heat destruction and venting to atmosphere. Mixture temperature, pressure and water vapor content are sensed during flow to the primary sterilization chamber and that sensed data is transmitted to a controller that directs operation of a plunger that travels into a water containing cylindrical vessel of a disposable syringe type device, that plunger travel forcing a measured amount of water from the cylindrical vessel that travels into a humidity chamber wherein the water is heated to a vapor state and is passed into the ozone-oxygen mixture flow. The ozone-oxygen mixture is humidified to within its saturation curve for its temperature and pressure, and which mixture temperature is maintained by line heaters under the direction of the controller to where it is passed into the primary sterilization chamber.

10 Claims, 6 Drawing Sheets

OZONE STERILIZATION SYSTEM VAPOR HUMIDIFICATION COMPONENT WITH DISPOSABLE WATER SOURCE

BACKGROUND OF THE INVENTION

1. Field of the Invention

This invention relates to medical instrument sterilization systems, and in particular to sterilization systems that utilize Ozone ($O_3$) as the sterilizing agent and provide for humidifying a sterilizing agent flow.

2. Prior Art

While humidification technologies have long been employed in the field of medical instrument sterilization, and even systems utilizing ozone ($O_3$) as the sterilization agent in such systems have previously been employed, and even some have provided for humidifying a flow of which sterilization agent. None, however, have provided for maintaining the relative humidity within the saturation curve of an ozone and oxygen gas mixture. Which saturation curve is the water vapor capacity of a mixture of oxygen and ozone gas at different variations in the gas mixture temperature, pressure, ozone concentration and gas flow rate. Unique to the present invention, the system controls water vapor content of a gas stream by monitoring its temperature, pressure and water vapor content utilizing thermistors and pressure transducers, along with a solid state humidity probe. A continual monitoring and adjustment establishes the precise water vapor content and delivery temperature of an ozone oxygen gas mixture at pressures which are requisite for sporicidal efficacy. The system of the invention provides for delivery of a stabilized oxygen-ozone gas mixture to even a remote container for sterilization usage, even when that gas flow is subjected to different environments as could alter flow conditions. Which water infusion is provided by a unique non peristaltic system of the invention which provides for incremental delivery of water to the vaporizer from a disposable vessel, thereby reducing any concern for cross contamination by elimination of standing water in the sterilization system.

The invention is preferably part of an ozone sterilization system that provides a separate containment system wherein the humidified ozone and oxygen mixture as a sterilizing agent is circulated to sterilize medical instruments. Which system provides for directing the humidified sterilization agent into a primary sterilization chamber that is separately sealed, is maintained within a second separate outer safety containment chamber, provides for monitoring conditions within both the primary sterilization and safety containment chambers, and is removable in its sealed state for transport. Though, of course, the invention is suitable for inclusion with another ozone sterilization system where a controlled gas humidification and disposable water delivery arrangement is appropriate.

Some examples of medical equipment sterilization systems that utilize heated ozone as the sterilization agent are shown in patents to Masuda, U.S. Pat. No. 5,120,512 and to Karlson, U.S. Pat. No. 5,069,880; and a plurality of container and chamber arrangements for use in sterilization processes utilizing treated ozone as the effluent are shown in patents to Anderson, et al, U.S. Pat. No. 5,118,471; and to Lutz, U.S. Pat. No. 5,087,419. None of which systems or arrangements provide for a precise gas conditions monitoring and appropriate water infusion from a disposable source to the gas flow to provide a precise water vapor content to maximize the sporicidal efficacy of the system.

SUMMARY OF THE INVENTION

It is a principal object of the present invention to provide an ozone sterilization system vapor humidification component with disposable water source to provide, within a medical instrument sterilization system that utilizes an ozone oxygen mixture as the sporicidal effluent, for an optimal mixture humidification for actual gas mixture conditions for maximizing the effluent sporicidal efficacy.

Another object of the present invention is to provide an arrangement for humidifying an ozone-oxygen mixture within the gas saturation curve by taking into account actual gas mixture conditions including temperature, pressure, ozone concentration and gas flow rate.

Another object of the present invention is to provide an arrangement for continually monitoring and adjusting water vapor content in an ozone-oxygen mixture flow that is delivered to a remote container.

Still another object of the present invention is to provide, a prepackaged disposable water source for injection into the ozone-oxygen mixture stream, providing a filtered sterile water source in a vessel wherein a plunger is arranged that is stepper motor operated to inject, on command, water from which vessel into the mixture stream, and which vessel is removed from the system for disposable in each sterilization cycle.

Still another object of the present invention is to provide an ozone sterilization system humidification component and disposable water source that will provide, during a medical instrument sterilization cycle, for passing a controlled flow of water for vaporization into an ozone-oxygen mixture flow to humidify that flow within the saturation curve of the mixture as determined by a monitoring of the flow temperature, pressure ozone concentration and flow rate, utilizing thermistors, pressure transducers, and a solid state humidity probe for automatically controlling a water injection from a prepackaged distilled water filled disposable vessel.

Still another object of the present invention is to provide a humidification component and disposable water source for inclusion with an ozone sterilization system that will operate within an automated system to provide to an ozone-oxygen mixture flow a water vapor input to provide a relative humidification of that flow within its saturation curve.

The invention is in a humidification component and disposable water source for an ozone sterilization system that includes a remote primary instrument sterilization chamber whereto the mixture of humidified ozone and oxygen is passed as a sporicidal effluent. The ozone sterilization system is contained within a console that provides a sealed section which constitutes a secondary safety chamber that contains the primary sterilization chamber, providing a safety barrier to a discharge to atmosphere of the ozone-oxygen sterilization agent during or after a medical instrument sterilization cycle of operation.

The ozone-oxygen sterilization agent is produced in an ozone generation tube by passage of an electrical current through oxygen, $O_2$, creating ozone, $O_3$, that, after cooling, is passed to the humidification component with disposable water source of the invention. The humidification component introduces a controlled amount of water into the mixture flow to provide a relative humidity in that flow that is within the saturation curve of the mixture. This water input heated to steam and its volume is varied with variation in temperature, pressure, ozone concentration and gas flow rate. The mixture flow characteristics are constantly monitored, during system operation, by sensors that include thermistors, pressure transducers, and a solid state humidity probe of the humidification component. Based on the data received from the sensors an incremental delivery of water is provided to the vaporizer under the control of a microprocessor that correlates the exit gas conditions and adjusted the water input to optimize the gas mixture humidification. For providing which incremental water delivery the invention provides a prepackaged syringe, or like vessel, that is filled with distilled water that is filtered sterile prior to its entry into the system by passing that flow through a filter that is arranged across the syringe exit port. The syringe includes a plunger that is urged into the syringe, forcing water therefrom, by movement of a stepper motor that is electronically operated by impulses as are sent from the micro-processor response to humidity sensing probe feedback. After sterilization cycle completion, the syringe is removed and replaced with a new syringe, eliminating a likelihood of cross contamination from a use of a standing water reservoir wherefrom water is drawn and passed into the sterilization system.

The humidified ozone-oxygen mixture is passed under pressure as a turbulent flow into the primary sterilization chamber where it scours and cleans a medical instrument or instruments therein during a sterilization cycle. Whereafter, the sterilization agent is vented to a destruction chamber wherein it is broken down into an inert state for venting to atmosphere.

After verification that both the primary sterilization and secondary safety chambers are free of sterilization agent or effluent, as determined by a timing out of timers connected to humidity sensors in both of which primary and secondary chamber, air under pressure is directed to a pneumatic actuator of the secondary chamber, unlocking which secondary chamber lid allowing it to be lifted to expose the primary sterilization chamber that contains the sterilized medical instruments. Which primary chamber is then disconnected from effluent in and out lines, at quick disconnect couplings, allowing for its removal and transport.

DESCRIPTION OF THE DRAWINGS

In the drawings that illustrate that which is presently regarded as the best mode for carrying out the invention.

DETAILED DESCRIPTION

Figure 1:
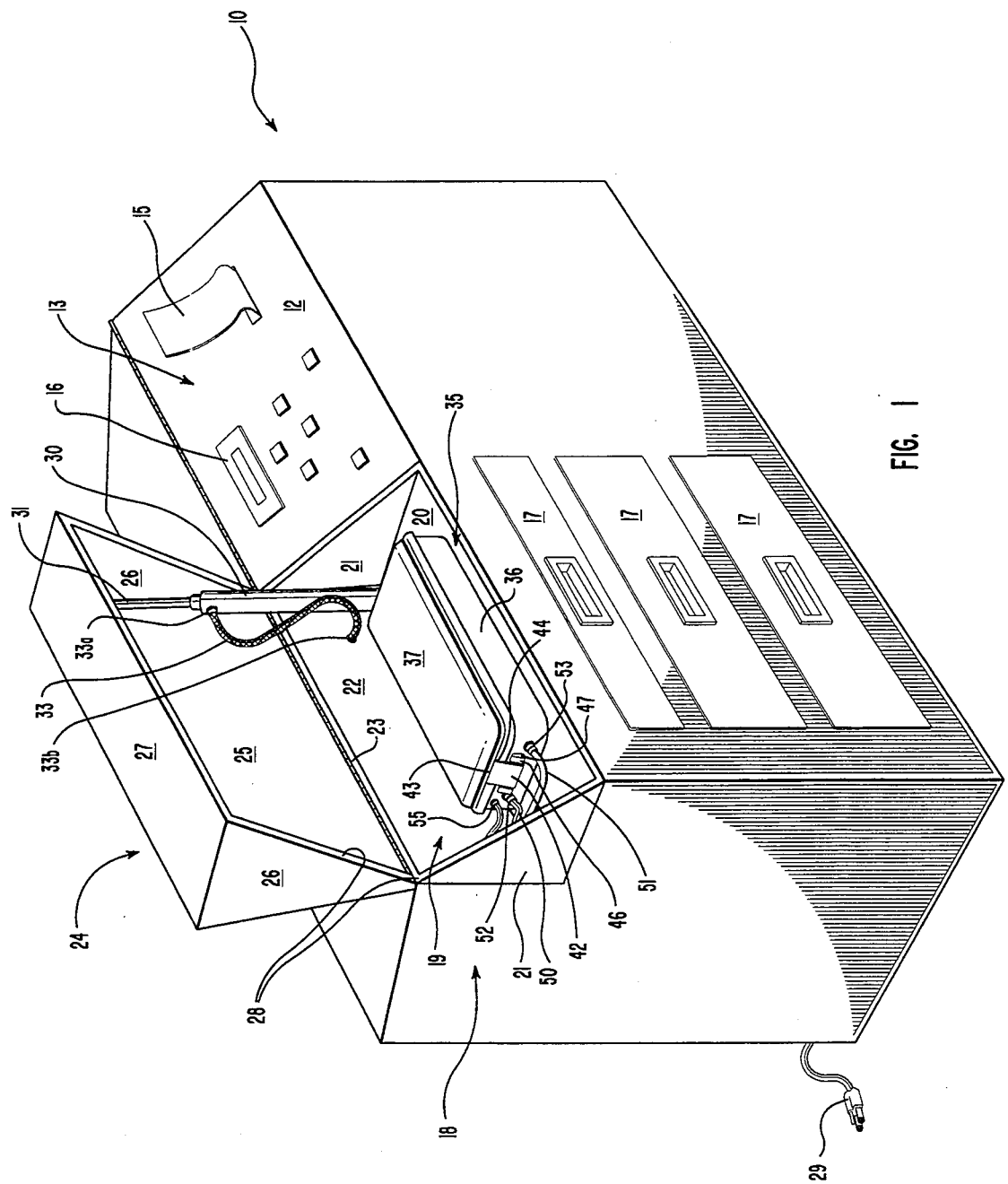
FIG. 1 is a profile perspective view of a console containing an ozone sterilization system, showing a clam shell type lid that covers over a top section of the console in an open attitude exposing a compartment that is a secondary safety chamber for containing a primary sterilization and transport chamber wherein medical instrument sterilization takes place.

FIG. 1 shows a console 10 that contains, as shown in the block flow schematic view of FIG. 3, a medical instrument sterilization system 11, hereinafter referred to as sterilization system, that utilizes ozone ($O_3$) as the sterilizing agent. The sterilizing agent is, in fact, a mixture of ozone ($O_3$) and oxygen ($O_2$) that is generated from medical grade oxygen in a generation tube 79, described below. The medical instrument sterilization procedure performed in the medical instrument sterilization system 11 is entirely confined within the console 10 and constitutes a reduction of a microbiological population for a variety of microbes, including viruses, from a microbe carrying surface to essentially a zero population. The medical instruments to be sterilized are contained with a rigid pressure vessel that is compatible with an exposure to ozone, which container is preferably arranged to be used to store and transport the processed instrument into an operating theater, whereat a tray containing the processed instruments is removed. A preferred primary sterilization chamber 35 is described below. The invention in a vapor humidification component arranged with a disposable water source is shown as a humidity chamber 83 with a water reservoir 84 in the block flow schematic of FIG. 3 and in detail in FIG. 6, and is for humidifying the sterilizing agent flow for introduction into the sterilization chamber 35.

Figure 2:
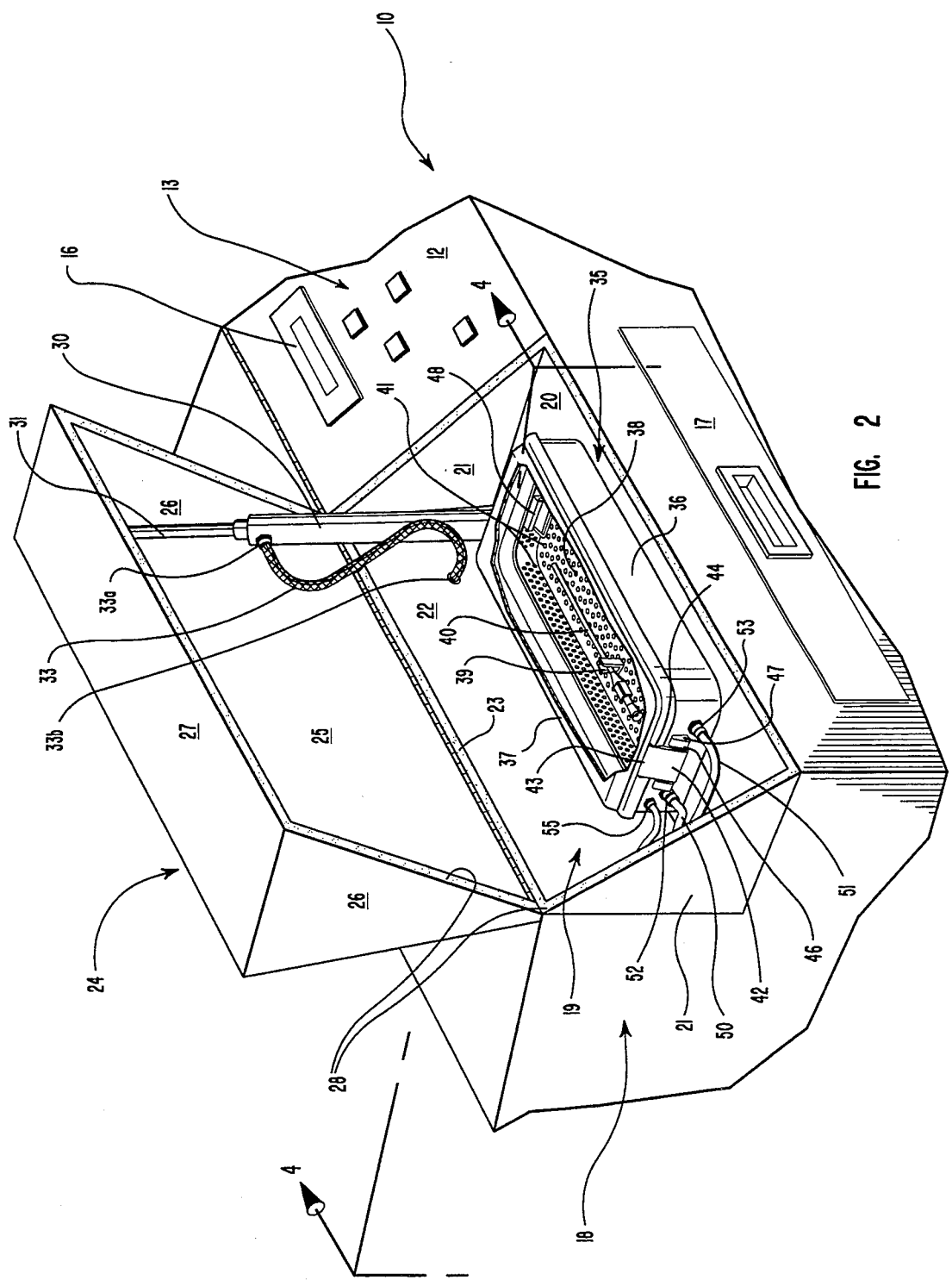
FIG. 2 is an enlarged view of a section of the console of FIG. 1, showing the clam shell type lid that includes a pneumatic piston arrangement for lifting and lowering which lid, and showing a section of the primary sterilization chamber lid broken away exposing a pan wherein medical instruments are arranged for sterilization.

FIGS. 1 and 2 illustrate console 10 for containing sterilization system 11 that incorporates the invention in a vapor humidification component 82, hereinafter referred to as humidification component, that, is shown best in FIG. 6, as including the humidity chamber 83 and water reservoir 84, described in detain hereinbelow. Though, it should be understood, the invention could be incorporated into a like sterilization system within the scope of this disclosure. The console 10 of FIGS. 1 and 2 is shown as having a sloping right side 12 that includes a control panel 13. The control panel 13 is shown also in the schematic of FIG. 3 as a number of buttons connecting through a programmable logic circuit (PLC) 14, that is shown also in FIG. 5. The control panel 13 buttons are for use by an operator who provides an input into the sterilization system 11 operation, with the programmable logic circuit (PLC) 14 processing that input to operate the sterilization system components, as set out below. In which system operation a printer 15 is connected to produce an output from the programmable logic circuit 14, providing a printed record of system operation. A display 16 is shown provided with which control panel 13 for providing a display or system readouts and time.

Figure 4:
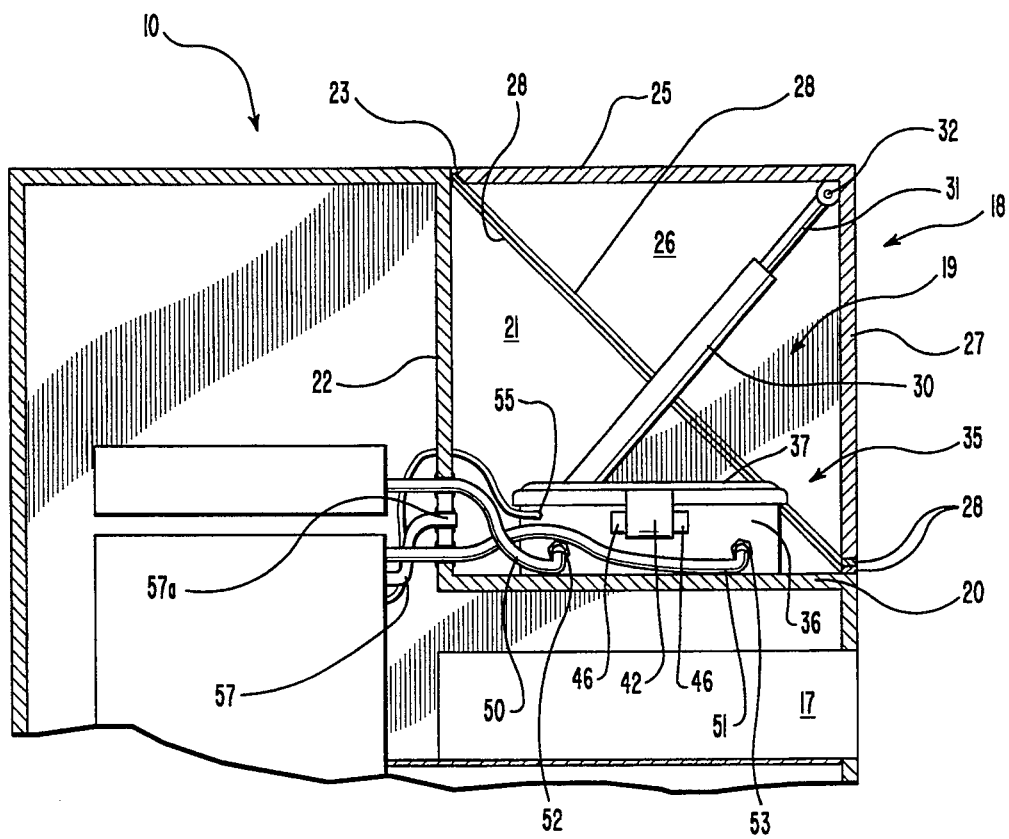
FIG. 4 is a side elevation sectional view taken along the line 4—4 of FIG. 2, only showing the clam shell type lid closed over the compartment.

As shown in FIG. 1, the left side of console 10, in a lower section thereof, includes a stack of drawers 17, for storage of system accessories, tools, and the like, and an electrical plug 29 is shown for connecting the system to a source of electricity. FIGS. 1, 2 and 4, show a secondary safety chamber 18, hereinafter referred to as secondary chamber, formed as a rectangular console compartment 19 that is located in the top left side thereof, alongside of the control panel 13. The compartment 19, with a clam shell type lid 24 fitted thereon, has a rectangular shape with identical flat bottom 20, and top 25, with right angle back and front walls 22 and 27 respectively, and side walls that are cut on the bias into sections 21 and 26, respectively. A top edge of the back wall 22 is connected through a hinge 23 to a rear edge of top 25. The clam shell type lid 24, hereinafter referred to as lid, is thereby formed by the top 25, side wall sections 26 and front wall 27, respectively. Lid 24 is a complement to the compartment 19 bottom portion that consists of bottom 20, side wall sections 21 and back wall 22. The lid 24 side wall sections 26 and front wall 27, respectively, edges are flush with and engage the edges of which compartment bottom portion side wall sections 21, back wall 22. Which compartment walls and the entire console 10 are preferably formed of steel panels with the joints sealed, though other suitable material could be used in their construction within the scope of this disclosure. Seals 28 are provided along the lid and compartment opposing surfaces for contacting one another when the lid 24 is closed, as shown in FIG. 4, for sealing the compartment 19 interior off from the surrounding area. Which seals 28, in practice are preferably a silicon sheet material such as a product known as Silastic, manufactured by General Electric Corporation.

The secondary chamber 18 is to be maintained in a closed sealed attitude during a sterilization cycle. To provide locking, of lid 24 over the console compartment 19, an actuator 30, that may to hydraulic or pneumatic, but is preferably pneumatic, is pivotally coupled at one end to the compartment 19 bottom 20 and includes a rod 31 extending outwardly from its opposite end. The rod end within the actuator 30 is secured to a piston, not shown, and is pivotally coupled on its opposite end at 32 to the junction of the lid top 25 and front wall 27, as shown best in FIG. 4. A pressure hose 33 is shown in FIGS. 1 and 2 connected at one end 33a into the actuator 30, proximate to the end wherefrom the rod 31 extends, and is fitted through the compartment 19 back wall 22 at 33b to connect to a source of air under pressure, not shown. When the sterilization system 10 is not in operation, the compressed air in the actuator acts as a brake against rod 31 travel, affording resistance to travel by an operator lifting or lowering the lid 24, pivoting around the hinge 23. When the sterilization system 10 is in operation, air under pressure is available in the actuator 30, urging the rod 31 into which actuator, to pull the lid 24 edges into close fitting contact with the compartment bottom portion edges, compressing the seal 28. The compartment interior is thereby sealed against leakage to atmosphere so long as the sterilization cycle is in process and so long as sterilization agent or effluent presence is sensed in the secondary chamber 18 or in a primary sterilization chamber 35, as set out hereinbelow.

As shown best in FIGS. 1 through 5, the secondary chamber 18 contains primary sterilization and transport chamber 35, hereinafter referred to as primary chamber. Shown best in FIGS. 1, 2 and 4, the primary chamber 35 is preferably a rectangular pan 36 arranged for covering by a lid 37, and, as shown best in FIG. 2, contains an instrument holding tray 38, hereinafter referred to as tray. Tray 38 may include an instrument mount 39 or mounts, for holding an instrument 40 during its sterilization, or may have a flat bottom surface, within the scope of this disclosure. All of which components are preferable formed from a rigid material, such as stainless steel, that is not affected by the sterilization agent or effluent that is used in the sterilization process carried on in which primary chamber 35. Preferably the tray 38 has a number of holes 41 formed through its bottom and side walls for promoting circulation of a sterilizing agent in, around and through the instrument 40, thoroughly cleaning and sterilizing all of the instrument 40 surfaces and crevices.

The lid 37 is for fitting, in sealing engagement, over the pan 36 during a medical instrument sterilization cycle and during transport of the primary chamber 35 containing sterilized medical instruments to an operating room wherein the seal is broken by operating room personnel, as discussed hereinbelow. To provide this sealed engagement, the opposing lid and pan edges are formed to overlay one another, fitting closely together, and, as needed, a seal is arranged between opposing lid and pan edges for providing an air tight seal when the edges are compressed together. Which seal is formed of a material that is not reactive with ozone, such as a silicon sheet material, such as Silastic, manufactured by General Electric Corporation, or a like material. In practice, as set out above, a preferred sterilization agent or effluent is ozone gas that has been humidified after formation and is at or near atmospheric pressure and standard or room temperature. Accordingly, the seal in both the primary and secondary chambers 35 and 19 is not required to contain high pressures or temperatures.

Pan handles 42 are provided on opposite pan ends for compressing the lid and tray edge together. Each pan handle 42 includes a hook 43, or bent over end, for fitting into a groove 44 that is formed into the center of an end section of a step formed around the lid 37. Each handle 42 opposite end is arranged for pivot coupling to the pan ends and is bent upon itself into a tube end, not shown. A pin 47 is fitted through the handle tube end, and through aligned holes or openings that are formed through a pair of piers 46 that are secured to and extend outwardly from the pan ends. So arranged, each handle 42 is free to pivot around pin 47 coupling with the pan 36 end, and is bowed outwardly across its center such that an operator can apply pressure to the bow, flexing it inwardly to where its hook end 43 will slid over the lid edge and into the groove 44. Whereafter, the operator releases pressure on the handle 42 that will then return to its original bowed state, drawing the hook end 43 into which lid edge groove 44, and pulling which lid edge into sealing engagement with the pan edge. The handles 42 pivot couplings through pins 47 maintained across piers 46 also provide gripping surfaces for facilitating an operator lifting the primary chamber 35 out from the secondary chamber 18 and carrying it to an operating room. Whereat the handles 42 are bent inwardly against their bow, releasing the lid 37, to expose the tray 38 therein. Which tray 38 is shown as including pivoting handles 48 secured to opposite ends for gripping for lifting the tray out from the primary chamber 35.

Medical instrument sterilization takes place in the primary chamber 35 that, as set out above, is removable from the secondary chamber 18 for transport in a sealed state to an operating room. Accordingly, both a sterilizing agent inlet line 50 and an exhaust line 51, as shown in FIGS. 1 through 5, are connected into the primary chamber pan 36 by quick release couplings 52 and 53, respectively. Which quick release couplings are preferably standard pneumatic hose type couplings, though other appropriate couplings could be so used, and an example of a quick release couple includes a male member that is secured to the end of the inlet or exhaust lines 50 or 51 is fitted into a female member secured across an opening into the pan 36. Which female member includes a spring loaded collar that is arranged for movement away from the male member, against its spring biasing, to release a ball contained in which female member to pass into a groove that is formed around which male member. With release of the female member collar the spring biasing returns the collar to its original attitude where the ball is prohibited from rolling out of the male member groove, locking the male and female members together. In operation, when the male member is released out of the female member, by moving the collar away from which male member, the opening through the female member is automatically closed. As shown best in FIG. 5, the quick release coupling 52 female member attaches to pass sterilizing agent from inlet line 50 into the primary chamber 35. The nozzle end provides a speeding up of a flow of sterilizing agent into the primary chamber 35, creating turbulence in that flow that is circulated throughout the chamber scouring and cleaning as well as sterilizing medical instruments therein.

Figure 5:
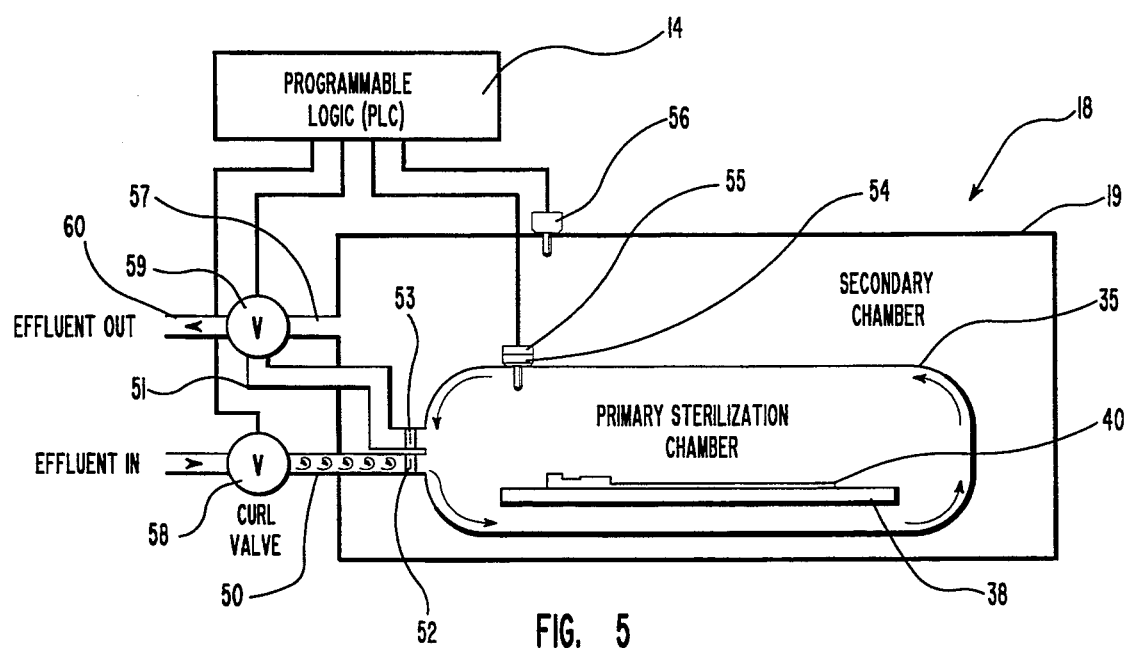
FIG. 5 is a side elevation schematic of the secondary safety chamber containing the primary sterilization chamber and showing sensors and gas valves operated by a programmable logic circuit.

Humidity probes or sensors 54 and 56, respectively, are provided for sensing humidified sterilizing agent presence in the primary and secondary chambers, 35 and 18, respectively. Within the scope of this disclosure the humidity probes or sensors 54 and 56 can be physically mounted in the primary and secondary chambers, 35 and 18, respectively, as shown best in FIG. 5, or can be arranged in the primary chamber exhaust line 51 and a secondary chamber exhaust line 57, as shown best in FIG. 3. Shown best in FIG. 4, the secondary chamber 18 exhaust line 57 end 57a is mounted in the secondary chamber back wall 22 wherethrough the primary chamber inlet and exhaust lines 50 and 51 are fitted and sealed. Both of which exhaust lines 51 and 57 connect into an effluent out line 60, as shown in FIGS. 3 and 5. Where the primary chamber 35 humidity probe or sensor 54 is for mounting into the pan 36, as shown in FIG. 5, it includes a base that extends beyond the pan surface. Which base is preferably a female electrical plug that is arranged for receiving and electrically coupling to a male electrical coupling 55 that is connected by wire, as is the secondary chamber humidity probe or sensor 56, into the programmable logic circuit (PLC) 14. Primary sterilization and secondary safety chamber humidity readings are provided to the PLC 14 that are utilized for controlling the chamber venting. The quick disconnect inlet and exhaust line couplings 52 and 53, respectively, and the humidity probe or sensor 54 and male coupling 55, facilitate the removal of the primary chamber 35 from the secondary chamber 18 after sterilization. The primary chamber 35 that contains sterilized medical instruments can then be transported, in a sealed state, to an operating room for opening by medical personnel. The primary chamber 35 is therefore both a sterilization vessel and transport container. For these dual roles, the primary chamber pan 36, lid 37 and tray 38 are preferably formed from an appropriate ridged material, such as stainless steel, that is not effected by the preferred sterilizing agent humidified ozone and is convenient to carry, utilizing handles 42, to an operating room.

Hereinabove has been set out a description of a primary sterilization and transport chamber 35 for containment in a secondary safety chamber 18 and its functioning in a sterilization cycle that is carried on in which primary sterilization chamber. It should, however, be understood that the invention can be included with a different arrangement of primary and secondary sterilization chambers than as set out above, or with a primary sterilization chamber alone, for providing humidified sterilization agent thereto, within the scope of this disclosure. As set out above, the sterilization cycle is automated under the control of the programmable logic circuit (PLC) 14 with an operator inputting information at control panel 13 buttons, with system functions shown at display 16, and with the PLC 14 receiving information from thermistors, pressure transducers, and a solid state humidity probe of the humidification component 82 of the invention for controlling injection of water from the water reservoir 84 for humidifying the mixture stream to within its saturation curve.

On starting the sterilization cycle, as illustrated in FIG. 5, the PLC 14 opens valve 58, identified as effluent in, to pass and circulate the humidified ozone-oxygen mixture to within the primary chamber 35. At the conclusion of which sterilization cycle, the PLC 14 operates an effluent out, valve 59 to vent both the primary and secondary chambers 35 and 18 through their respective exhaust lines 51 and 57, into an effluent out line 60. In practice, the respective primary and secondary chamber humidity probes or sensors 54 and 56 must sense an absence of the humidified sterilization agent in both of the chambers before the PLC 14 will release the actuator 30 that allows for opening of the secondary chamber lid 24, for removal of the primary chamber 35.

Figure 3:
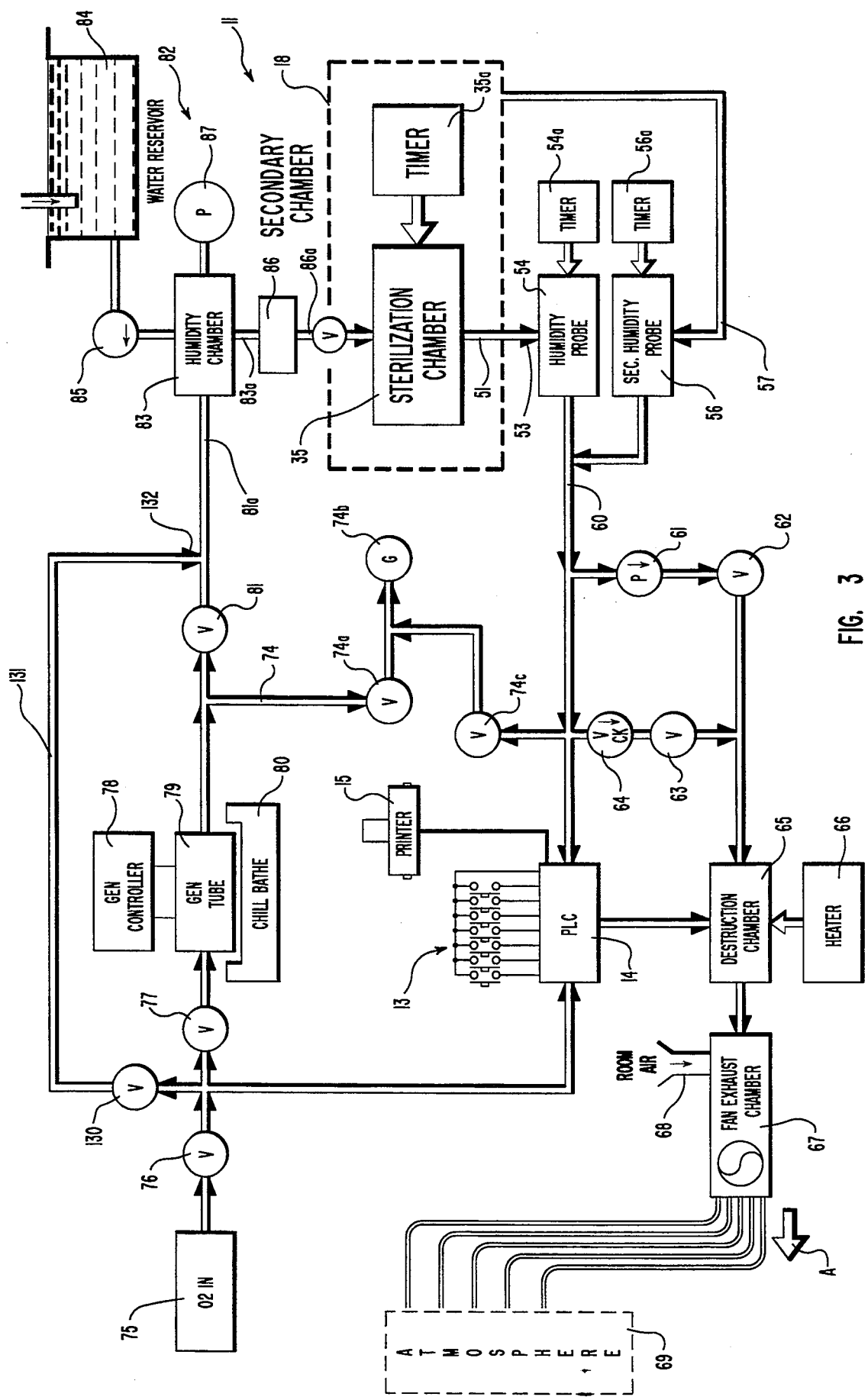
FIG. 3 is a block flow schematic of the ozone sterilization system showing the secondary safety chamber in broken lines.

In the effluent venting process, as illustrated by the block flow schematic of FIG. 3, effluent from the primary and secondary chambers 35 and 18 is pulled through the effluent out line 60 by pump 61, that flow passing through valve 62 and into a destruction chamber 65. Additionally, for controlling effluent passage for destruction, the effluent out line 60 connects to the PLC 14 for provide a sensing of effluent presence, and is joined to an ozone emergency venting line 74. Which line 74 extends from an ozone generation tube 79 that connects through valves 74a and 74c and contacts an in line pressure gauge 74b. Which pressure gauge 74b is electrically connected to provide pressure data to the PLC 14. The junction of the effluent out line 60 with the ozone emergency venting line 74 connects through a check valve 64 and valve 63 to vent ozone and humidified ozone into the destruction chamber 65. The destruction chamber 65, in turn, utilizes a heater 66 to heat the received humidified ozone or ozone alone, breaking down the received ozone into an inert state, that is pulled by a fan into a fan exhaust chamber 67. The fan exhaust chamber mixes the received oxygen with room air that enters through port 68 and the mixture is then vented, illustrated by arrow A, to atmosphere, as shown as a broken line box 69. So arranged, an operator is protected from a sterilization agent exposure both during the sterilization cycle and during venting operations.

The described medical instrument sterilization system, as set out above, employs an ozone-oxygen mixture and the sterilization agent or effluent, as set out above, which mixture is preferably humidified. For producing the humidified ozone-oxygen mixture flow, as illustrated in FIG. 3, oxygen, that is preferably medical grade oxygen, is illustrated as block 75, is passed through valves 76 and 77 and into a generation tube 79. The generation tube 79 is controlled by a generation controller 78 and is arranged within a chill bathe 80 for maintaining the produced ozone-oxygen mixture at or near atmospheric pressure and room or standard temperature conditions. On opening of valve 81, the ozone-oxygen mixture from generation tube 79 passes through a transfer line 81a to humidity chamber 83 of humidification component 82 of the invention. A water reservoir 84 is shown for supplying water, under pressure generated by a stepped motor and actuator combination 85, to the humidity chamber 83 at a rate as controlled by the PLC 14, as set out and described in detail hereinbelow with respect to a discussion of FIGS. 6 and 7.

Shown in FIG. 3 the humidification component 82 of the invention consists of the humidity chamber 83 and water reservoir 84, along with a stepper motor actuator combination 85 for supplying a measured amount of water to the humidity chamber, and a pump 87 for urging a humidified ozone-oxygen mixture from the humidity chamber, through a sensor block 86, and through a line 86a to the sterilization chamber 35. Which sensor block 86 sensing conditions within the mixture flow and transmits that information to the PLC 14 for controlling water input to the humidification chamber 83 and heating of the ozone-oxygen mixture as it flows to the sterilization chamber 35, providing a humidified sterilization agent that is optimum for efficiently and completely sterilizing medical instruments as are contained in which sterilization chamber 35. Which humidification component 82 is described in greater detail hereinbelow with reference to FIGS. 6 and 7.

Figure 6:
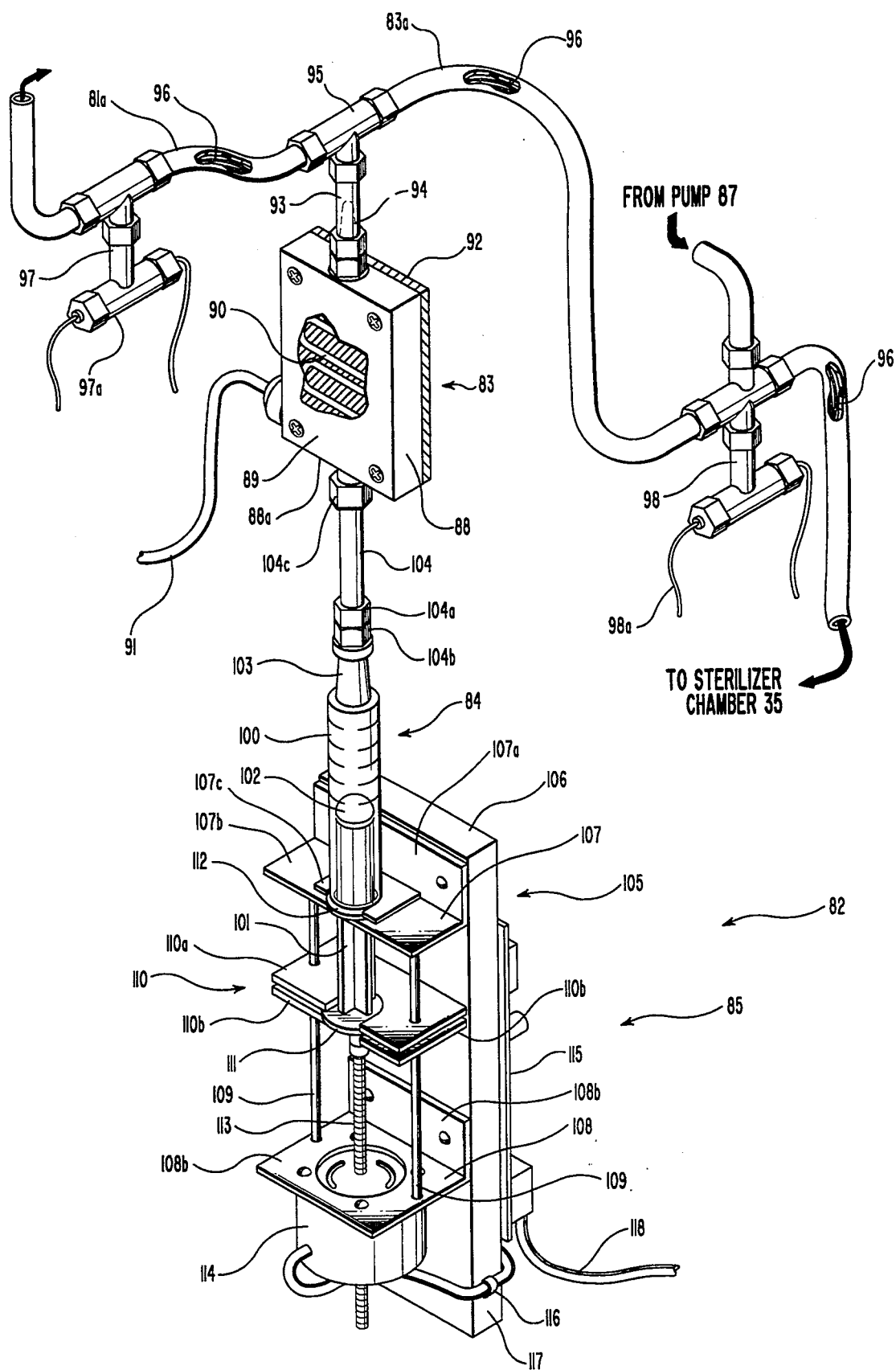
FIG. 6 is a profile view of a humidity chamber and water reservoir arrangement of the humidification component of the invention.
Figure 7:
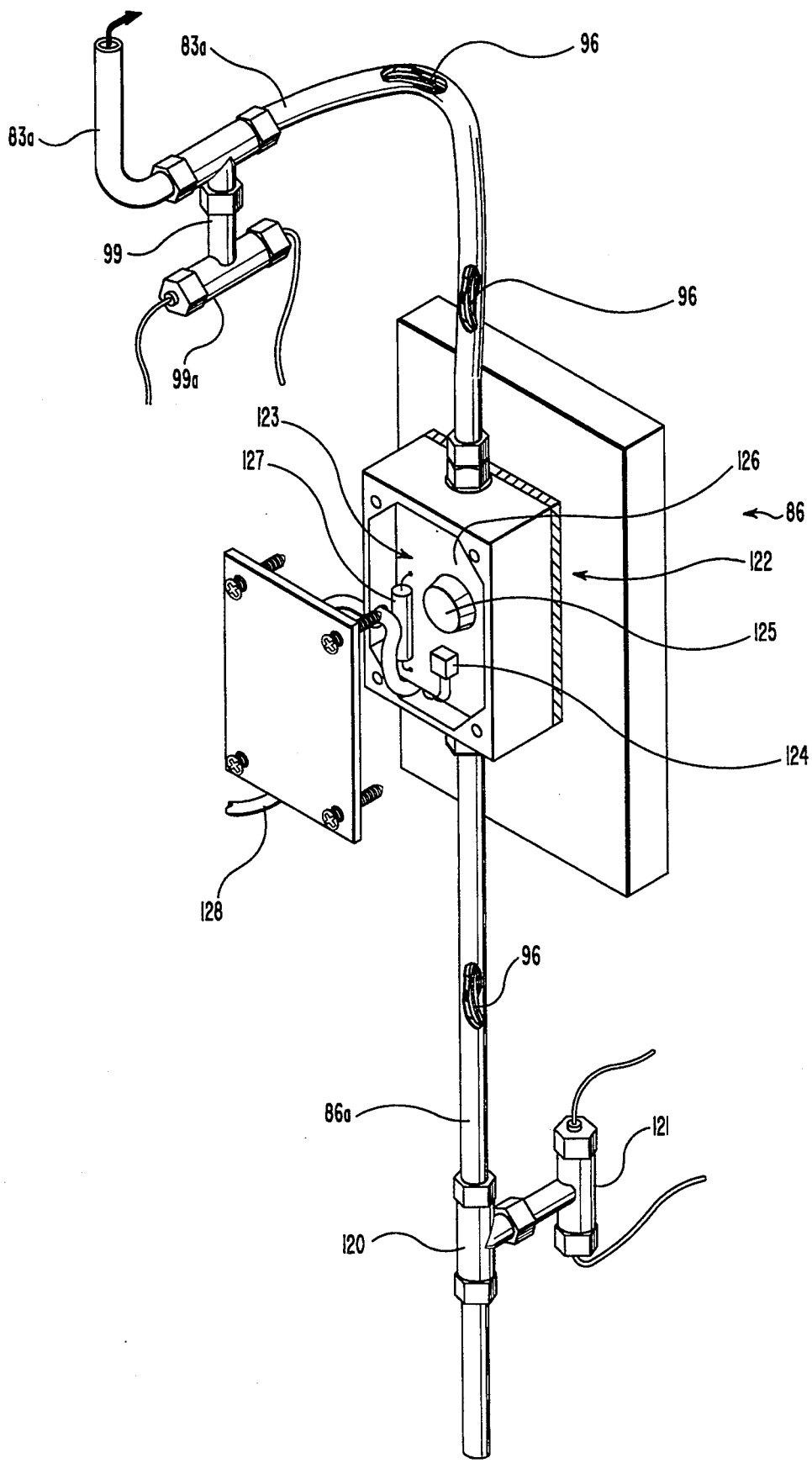
FIG. 7 is a profile view of a sensor block of the humidification component arranged between the humidity chamber and the primary sterilization chamber containing sensing devices for measuring the actual ozone-oxygen mixture conditions of temperature, pressure and water vapor content.

In FIG. 6 the humidification chamber 83 and water reservoir 84 are shown removed from the humidification component 82, with FIG. 7 showing the sensor block 86 separated from the humidification chamber 83 and removed from which humidification component 82. In FIG. 6, the humidification chamber 83 is shown as a narrow rectangular heating block 88 with a section removed from a forward face 89 thereof exposing a center cavity 90. The heating block 88 is formed of an electrically conductive metal, such as aluminum and is connected to a source of electrical current through a cord 91. In practice, the heating block 88 interior cavity 90 is maintained at approximately one hundred twenty (120) degrees Celsius, plus or minus twenty (20) degrees Celsius, for turning an injection of water into water vapor, which temperature can be closely controlled by the PLC 14 that turns off and on electrically current passage thereto through cord 91. For mounting in the console 10, the heating block 88 is preferably backed with a heat insulative backing 92 for engaging a console interior surface.

The water injected into the heating block 88 expands as it is converted to water vapor and is thereby under pressure in the cavity 90, and expands into a line 93 that may contain a nozzle 94, shown in broken lines, that connects into a center leg of a T connector 95. The T connector 95 connects between line 81a downstream from valve 81 from the ozone generator, wherethrough an ozone-oxygen mixture is passed, and a line 83a that connects to sensor block 86. The water vapor from the heating block 88 is passed into the ozone-oxygen mixture flow, mixing thoroughly therein, to humidify that mixture to its water vapor carrying capacity as governed by the mixture flows temperature, pressure and ozone and oxygen concentrations. To promote mixing, the water vapor mixture may be passed through the nozzle 94, shown in broken lines into a mixture flowing through a constant diameter straight tube of T connector 95, or T connector 95 may itself include a nozzle, not shown producing a turbulent flow downstream of which nozzle wherein the water vapor is injected, either arrangement for providing a full and complete mixing of the injected water vapor with the ozone-oxygen mixture stream, fully humidifying that flow. For maintaining a constant temperature of the ozone-oxygen mixture before and after humidification and to where it passes into the sterilization chamber 36, the lines, 81a, 83a and 86a into the sterilization chamber all included embedded wires 96 that receive an electrical current flow to the individual section of wires in lines 81a, 83a, and/or 86a, as directed from the PLC 14 based upon mixture conditions as measured and passed to which PLC 14 from thermistors arranged at points along which lines, shown in FIGS. 6 and 7, as, respectively, ozone-oxygen mixture thermistor 97 linked by a sensor circuit 97a to the PLC 14, a humidified mixture thermistor 98 linked by a sensor circuit 98a to the PLC 14, and a chamber gas thermistor 99 linked by a sensor circuit 99a to the PLC 14, as discussed hereinbelow.

As set out above, the water reservoir 84 is for providing a measure amount of water to the humidification chamber 83 for conversion into water vapor for injection into the ozone-oxygen mixture stream to humidify that stream to where the relative humidity is within the stream saturation curve. For providing that closely controlled water injection the water reservoir 84 preferably is an arrangement for injecting a closely measured volume of water on command. To meet this requirement, the water reservoir 84, shown best in FIG. 6, is a hypodermic type arrangement of a cylindrical vessel 100 wherein a plunger 101 is arranged to slide longitudinally. A top or head end 102 of which plunger is arranged to provide a water tight seal against the interior wall of the cylindrical vessel 100, pushing water ahead of head end as the plunger 101 is urged into cylindrical vessel 100. Plunger travel forces water contained in which cylindrical vessel through a nozzle end 103 that travel through a line 104 and is sprayed into and vaporized in the humidity chamber 83. The cylindrical vessel 100 and plunger 101, as set out below, are removable from providing a water source that is disposable to be replaced by a filled vessel after each sterilization cycle, thereby reducing any likelihood of cross contamination.

A frame 105 is provided for releasably mounting the cylindrical vessel 100 and plunger 101 to operate as set out above. The frame 105 include a mounting plate 106 that mounts within the console 10 and provides for points of attachment to a stationary upper plate 107 and a spaced apart stationary lower plate 108. Which stationary upper and lower plates are shown as right angle brackets, with upright legs 107a and 108a, respectively, that are each shown secured to the mounting plate 106, with horizontal legs 107b and 108b of which stationary plates are shown as parallel to and spaced apart from one another. Extending between the horizontal legs 107b and 108b are arranged a pair of spaced slide rods 109 that support, to slid therealong, a movable middle plate 110 that consists of upper and lower sections 110a and 110b, respectively. The upper and lower sections 110a and 110b are for clamping therebetween an edge of a flat thumb engaging end 111 of plunger 101, movement of which movable middle plate 110 along slide rods 109 to move the plunger 101 into or out of the cylindrical vessel 100.

As set out above, the water reservoir 84 is preferably removable and replaceable within the sterilization system 11. For releasable mounting the water reservoir cylindrical vessel 100 to provide for travel of the plunger 101 therein, a lip edge 112 of the cylindrical vessel is fitted into an arcuate opening in a coupling plate 107c of the horizontal leg 107b of the stationary upper plate 107, the lip edge 112 to be slid under the edge of the coupling plate 107c arcuate opening and clamped between it and the upper surface of the horizontal section 107b. So arranged, the cylindrical vessel 100 is supported to the stationary upper plate 107 with the plunger 101 to travel up and down therein with movement of the moveable middle plate 110.

The cylindrical vessel 100, as set out above is connected at its nozzle end 103 to inject a controlled volume of water through line 104 into the humidification chamber 83. Which cylindrical vessel nozzle end 103 mounting to an end of line 104 is shown as a stack of top nut 104a and bottom nut 104b, the bottom nut 104b secured to turn freely across the nozzle end 103 and is for turning onto a threaded sleeve end, with the top nut 104a for turning onto the threaded sleeve opposite end. The cylindrical vessel nozzle end is thereby secure to the line 104 by the combination of the threaded sleeve and top and bottom nuts, with the line 104 opposite end shown secured by turning of a nut 104c onto a threaded sleeve 88a that extends from the bottom of the humidification chamber 83 heater plate 88. The arrangement of which bottom nut 104b for turning onto the threaded sleeve and the clamping of the cylindrical vessel lip edge 112 between the stationary upper plate horizontal leg 107b and the clamping plate 107c along with the plunger flat thumb engaging end 111 to the movable middle plate 110 provides for a quick disconnect coupling of the cylindrical vessel 100 into and out of the sterilization system 11.

The plunger 101, as set out above, is fitted for travel within the cylindrical vessel 100, urging water therefrom under control of the PLC 14, to provide a controlled input of water to the humidity chamber 83. For providing a controlled incremental movement of the plunger 101 an end of an actuator rod 113, that is a threaded rod, is fitted to the movable middle plate 110, with vertical travel of which actuator rod 113 to move the plunger in cylindrical vessel 100. To provide actuator rod 113 movement, it is turned through a linear actuator 114 that is mounted to the undersurface of the horizontal leg 108b of the lower mounting plate 108, the actuator rod extending vertically therefrom through a center cavity through which horizontal section. For providing extension of the actuator rod 113 out from the linear actuator 114, moving the plunger 101, a control panel 115 that is secured to the rear of the mounting plate 106 receives command and control signals through a line 118 from the PLC 14 and passes power through line 117 into a stepper motor of the linear actuator 114 that extends actuator rod 113 therefrom. As shown, the line 117 is maintained onto the side of the mounting plate 108 by a clip 116 that secures the line thereto as it extends from the control panel to the linear actuator. Incremental movement of the plunger 101 into the cylindrical vessel is thereby provided to urge a controlled volume of water therefrom to the humidity chamber 83 so as to maintain the humidity level of an ozone-oxygen mixture within its saturation curve.

As shown in FIG. 3, and as set out above, the humidified ozone-oxygen mixture is passed out from the humidity chamber 83, as urged by pump 87 into the sensor block 86 and thence to the sterilization chamber 35. The lines wherethrough the ozone-oxygen mixture passes to the sterilization chamber are preferably heated by wires 96 contained in which lines, shown in FIGS. 6 and 7 such that the gas mixture will just hold the moisture introduced therein by the humidity chamber as it travels into the sterilization chamber. Mixture temperature conditions are accordingly monitored by the ozone-oxygen mixture thermistor 97, the humidified mixture thermistor 98, and the chamber gas thermistor 99, that pass mixture temperature data to the PLC 14 via sensor circuits 97a, 98a, and 99a, respectively. Thermistor devices are well known and a number are suitable for use in practice as the thermistors of the invention. The PLC thereby directing mixture flow heating as well as controlling mixture humidification. The sensor block 86 is provided for finally checking the ozone-oxygen mixture conditions of temperature and humidity prior to its passage through a line 86a that includes heat wires 96, through a sterilization chamber valve 120 that is itself heated by valve heater 121, and into the sterilization chamber 35. To provide which temperature and humidity sensing, the sensor block 86, that is shown in FIG. 7 as having had a front panel removed, includes a relative humidity block 122. The relation humidity block 122 further includes a PC board 123 that is electronically linked to the PLC 14, for providing constant mixture humidity readings. For monitoring mixture heat the PC board includes a relative heat sensor thermistor 124, that is like the thermistors described above, is arranged immediately adjacent to a passage 125 formed through a center divider board 126 wherethrough the mixture flow is directed through the sensor block, exiting into the line 86a the connects to valve 120. Additionally, the PC board 123 includes a heating resistor 127 is provided alongside of the center divider board passage 125, also for monitoring mixture head conditions, with the temperature and humidity data so collected passes through cable 128 to the PLC 14 that acts on which information for adjusting ozone-oxygen mixture conditions.

The optimized ozone-oxygen mixture that is passed through from the sensor block 86 travels through the heated valve 86a, shown in FIG. 3, and into the sterilization chamber 35, scouring and sterilizing, as described, medical instruments maintained therein.

In practice a ozone-oxygen mixture entering the sterilization chamber 35 is preferably at a temperature of approximately thirty one (31) degrees Celsius (C.), with an ozone concentration of approximately twelve (12) percent ozone, to ten (10) percent water, plus or minus three (3) percent, to oxygen. The humidified ozone is passed from line 86a through line 50 into the sterilization chamber 35, as set out hereinabove. Which humidified ozone is preferably at or near atmospheric pressure and room or standard temperature. The low temperature and pressure state of which ozone-oxygen mixture as is introduced into the sterilization chamber 35 greatly simplifies sterilization operations as the sterilization chamber is required only to contain low temperature and pressure of gas, thereby simplifying the sealing requirements of both the primary sterilization and secondary safety chambers 35 and 18, respectively.

For start-up and for controlling ozone concentrations during operations, as illustrated in FIG. 3, valve diversion 130 may be opened for routing oxygen around the ozone generation tube 79. With diversion valve 130 open, oxygen passes through line 131 to junction 132 with line 81a, and to the humidity chamber 83. Oxygen may therefore also be conveniently utilized for providing system purging after suspension of ozone generation. In the event of a termination of the sterilization cycle prior to completion it is, of course, necessary to remove the ozone sterilization agent from the system. This is accomplished by shutting down the ozone generation tube 79 and closing valve 81. In which shut down state oxygen is preferably routed, as set out above, to the humidity chamber 83. The ozone generator is thereby bypassed, to purge the sterilization chamber 35. For venting ozone as is present in the generation tube 79 and connecting lines, through a line 74, a valve 74a is opened and ozone presence in the generation tube and lines is monitored by pressure gauge 74b. Opening of a valve 74c allows for continued effluent passage in line 74 to both the PLC 14, for monitoring and control, and through the check valve 64 and valve 63 for destruction in the destruction chamber 65, as set out above.

Timers 54a and 56a are provided for monitoring component operations during a sterilization cycle that are connected, respectively, to the humidity probe 54, that senses humidified ozone presence in the sterilization chamber 35, and to secondary humidity probe 56, that monitors humidified ozone presence in the secondary chamber 18. The timers 54a and 56a are started when the humidity probes indicate an absence of humidified ozone, for continuing the system purging for a period of time to insure a full evacuation of humidified ozone from the primary and secondary chambers prior to system opening. Further, a timer 35a is provided that is set by an operator to a time period of the sterilization cycle for the particular medical instruments to be sterilized. Which primary sterilizer chamber timer 35a is programed and that setting is passed to the PLC 14 for setting the periods for system component functioning.

While a preferred form and embodiment of our invention in an ozone sterilization system vapor humidification component with disposable water source and its functioning in an ozone sterilization system has been shown and described herein it should be understood that the present disclosure is made by way of example only, and that variations and changes can be made thereto without departure from the subject matter coming with the scope of the following claims, and a reasonable equivalency thereof, which claims should be regarded as our invention.

We claim:

1. A vapor humidification component with a disposable water source in combination with a medical instrument sterilizer with an ozone generator comprising, a humidification chamber that is a block body and is arranged as a component of a medical instrument sterilizer with an ozone generator, which said block body is open therethrough and includes a heater means for vaporizing a volume of water injected through a water inlet line that is then passed out of said block body through a vapor exhaust line for mixing into an ozone-oxygen mixture flow; an ozone-oxygen mixture flow; an outlet line connected to receive said vapor exhaust line and to a sterilization chamber where through said ozone-oxygen mixture flows; a water reservoir means for connection to and for injecting a measured volume of water into said humidification chamber that includes a vessel for containing water and a plunger means for movement in said vessel for urging water therefrom into said water inlet line of said humidification chamber, said vessel and plunger means to be removable for disposal and replacement; means for moving said plunger means into said vessel to pass a controlled volume of water therefrom into said humidification chamber water inlet line; means for sensing temperature and humidity conditions of said ozone-oxygen mixture flow; means for heating said ozone-oxygen mixture flow; and means for controlling said means for heating said ozone-oxygen mixture flow and said plunger means travel for providing a humidification of said ozone-oxygen mixture flow that is within the saturation curve of said ozone-oxygen mixture.

2. A vapor humidification component as recited in claim 1, wherein the block body is a rectangular block of metal that contains a central cavity and is open therethrough between the water inlet and vapor exhaust lines and is connected to a source of electrical energy for heating water injected therein to its vaporization temperature when an electrical current is passed thereto; and means for connecting said rectangular block of metal to said electrical current.

3. A vapor humidification component as recited in claim 2, further including a heat insulative plate for mounting to a back surface of the rectangular metal block said heat insulative plate providing a mounting point within the medical instrument sterilizer; and a nozzle means arranged in the vapor exhaust line for spraying water vapor into the ozone-oxygen mixture flow.

4. A vapor humidification component as recited in claim 1, wherein the vessel and plunger means is a conventional hypodermic, except that a hypodermic needle thereof has been replaced with a releasable coupling means for connection to the water inlet line, said conventional hypodermic arranged to be removed and replaced after each use in a sterilization cycle; the plunger means is engaged by a screw means that, when said screw means is turned, moves said plunger means into said vessel; and means for turning said screw means.

5. A vapor humidification component as recited in claim 4, wherein the conventional hypodermic is arranged between a pair of right angle brackets that each have an outstanding leg and a flat mounting leg for fitting onto a mounting plate, and one of said right angle brackets flat mounting leg is fixed onto said mounting plate with its outstanding leg configured to receive the vessel of said conventional hypodermic fitted thereto, with the second right angle bracket mounted at its flat mounting leg to said mounting plate, and with a plurality of rods secured between the right angle bracket outstanding legs; and a plate arranged to be moveable along said plurality of rods and is in engagement with a thumb engaging end of said plunger means to move said plunger means in said vessel; and the screw means is in engagement with and, when turned, moves said plate and said plunger means.

6. A vapor humidification component as recited in claim 5, wherein the screw means is a threaded rod that is turned through a linear actuator that is rigidly mounted to the mounting plate; and the means for turning said screw means is a stepper motor that is arranged in said linear actuator.

7. A vapor humidification component as recited in claim 1, wherein the means for heating said ozone-oxygen mixture flow are a number of heat wires that are arranged in the humidification chamber outlet line connecting to the sterilization chamber wherein said number of heat wires are connected to a source of electrical current that, when passed into said number of heat wires, generate heat.

8. A vapor humidification component as recited in claim 1, wherein the means for controlling is a programmable logic circuit that electrically connect to the means for sensing temperature and humidity, said programmable logic circuit to receive temperature and humidity data and act on said data to pass electrical current to individual heat wires for heating the ozone-oxygen mixture flow and operate the means for moving the plunger means in said vessel for urging a volume of water from said vessel into the water inlet line.

9. A vapor humidification component as recited in claim 8, wherein the means for sensing are thermistors that are arranged at intervals in the humidification chamber outlet line downstream from the humidity chamber, with a sensor block that includes a relative humidity sensor that is electrically connected to supply flow humidity data to the programmable logic circuit.

10. A primary sterilization and transport chamber as recited in claim 1, wherein the ozone content of the ozone-oxygen mixture that is passed to a primary sterilization chamber of the medical instrument sterilizer system is approximately thirty one (31) percent with ten (10) percent water vapor as compared to said mixture oxygen content.

* * * * *